United States Patent [19]
Bergersen

[11] Patent Number: 5,194,004
[45] Date of Patent: Mar. 16, 1993

[54] METHOD OF INJECTION-MOLDING SLOW RELEASE FLUORIDE

[76] Inventor: Earl O. Bergersen, 950 Green Bay Rd., Winnetka, Ill. 60093

[21] Appl. No.: 740,802

[22] Filed: Aug. 6, 1991

Related U.S. Application Data

[63] Continuation-in-part of Ser. No. 374,662, Jun. 30, 1989, Pat. No. 5,037,294.

[51] Int. Cl.$^5$ .............................................. A61C 13/00
[52] U.S. Cl. ........................................ 433/215; 264/16
[58] Field of Search ..................... 433/6, 215; 264/16

[56] References Cited

U.S. PATENT DOCUMENTS

| | | | |
|---|---|---|---|
| 3,848,335 | 11/1974 | Bergersen | 433/6 |
| 3,939,598 | 2/1976 | Bergersen | 433/6 |
| 4,044,762 | 8/1977 | Jacobs | 433/6 |
| 4,376,628 | 3/1983 | Aardse | 433/217.1 |
| 4,772,325 | 9/1988 | Kwan et al. | 433/215 |
| 4,784,605 | 11/1988 | Bergersen | 433/6 |

OTHER PUBLICATIONS

"Continuous Fluoride Release from Removable Appliances", by Dr. Miethke et al. JCO, Aug. 1988, pp. 490-491, vol. XXII, No. 8.

Modern Plastics Encyclopedia Issue 1956, pp. 592-593, Sep. 1956, vol. 34, No. 1A, Plastics Catalogue Corp., Bristol, Conn.

Modern Plastics Encyclopedia 88, pp. 7-8, Oct. 1987, vol. 64, No. 10 A, McGraw-Hill, Inc. N.Y., N.Y..

"TP Laboratories, Inc." brochure, 1974, gingival conditioner, orthopedic splint, varsity guard.

Primary Examiner—John J. Wilson
Attorney, Agent, or Firm—Hill, Van Santen, Steadman & Simpson

[57] ABSTRACT

A human detention appliance or pacifier device or anti-thumb sucking device is made by a method of injection molding whereby a charge of fluoridating material is admixed with a high-temperature solvent, and then tumbled with a base thermoplastic molding material to form a pre-fluoridated mixture stable which is stable within the temperatures necessary to melt the mixture and the high-temperature limit of the high-temperature solvent, and physically embodied in the molding so that when used, the fluoridating material will leach out of the appliance and become mixed with fluids in the mouth at the buccal, labial, lingual and occlusal surfaces of the teeth which come in contact with the appliance.

9 Claims, 1 Drawing Sheet

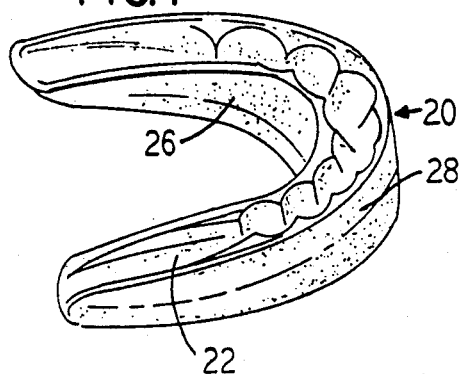
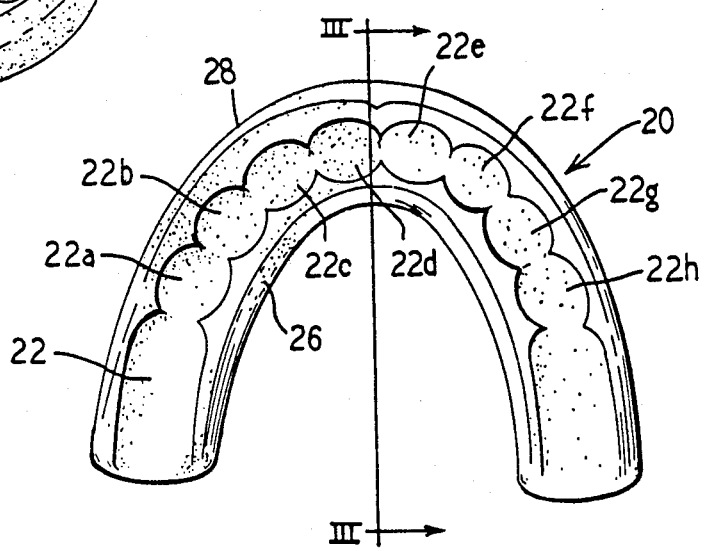
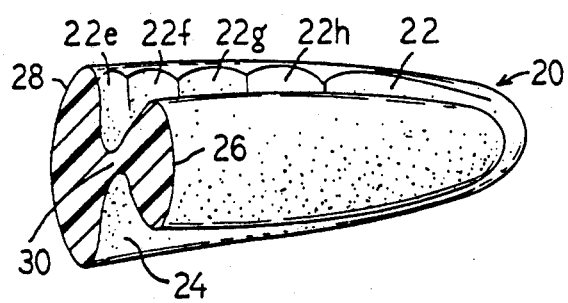
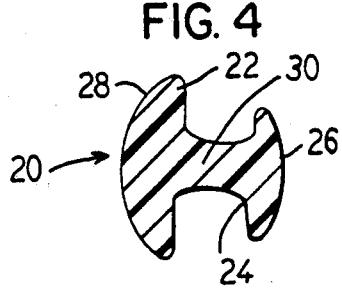
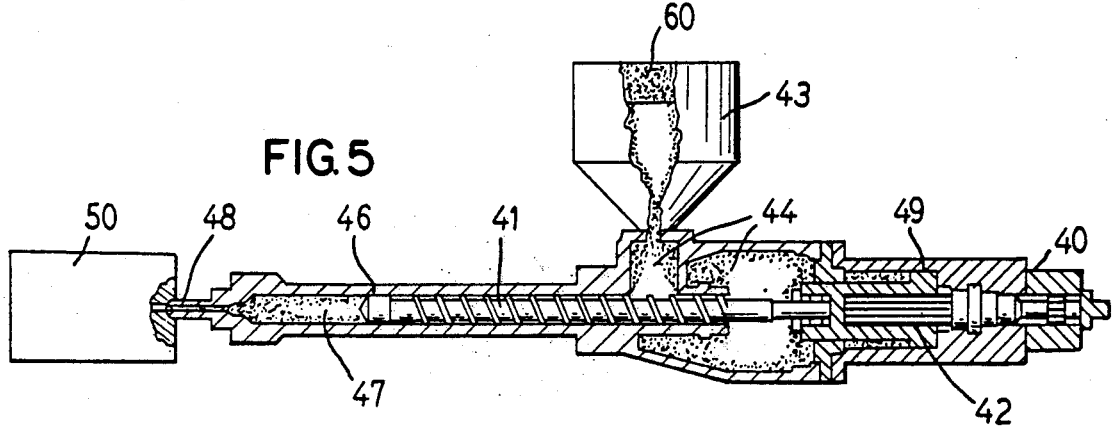

METHOD OF INJECTION-MOLDING SLOW RELEASE FLUORIDE

CROSS-REFERENCE TO RELATED APPLICATION

The invention is a continuation-in-part of the U.S. application entitled "Method of Injection-Molded Slow Release Fluoride And A Human Dentition Appliance Formed Thereby", U.S. Ser. No. 374,662, filed Jun. 30, 1989, now U.S. Pat. No. 5,037,294.

BACKGROUND OF THE INVENTION

1. Field of the Invention

This invention relates to oral appliances including appliances for correcting human dentition, and more particularly relates to a method of injection-molding slow release fluoride and tin or other preventive chemicals into a human or animal dentition appliance for effecting the protection of teeth and supporting tissues by fluoridation and bacteriostatic action, and by incorporating these same chemicals into heat molded plastics that can in turn be used in vacuum forming appliances and incorporating chemicals into any soft or hard plastics or rubber used in fabricating custom positioners and other appliances made by vacuum and/or heat forming or injection molding or by other molding processes such as rotary molding and blow molding.

2. DESCRIPTION of the RELATED ART

The World Health Organization recommends a fluoride ion level for 1.3 mg. per day based on fluoride exchange via internal metabolism. Fluoride has heretofore been put into toothpaste, tooth filling material and even into powdered self-curing acrylic for retainers. Other materials such as ink and scents such as peppermint and other flavors have been injection molded into orthodontic appliances.

SUMMARY OF THE INVENTION

The present invention contemplates the injection molding of fluoride into a human dentition appliance by supplying a charge of molding material or base material and admixing with the base material, by tumbling, a charge of a mixture, including a fluoridating material and a high-temperature solvent, to form a pre-fluoridated mixture.

The pre-fluoridated mixture is then melted at softening temperatures, within the high-temperature limit of the high-temperature solvent, to form a melt. The melt is injected into a relatively cool mold, shaped to form a molding in the configuration of a human dentition appliance. It is also possible to form the dentition appliance from sheets of material to be re-heated and formed over a model of the teeth. The dentition appliance could also be formed by any molding method, such as, for example, a rotary molding or blow molding. The mold is then chilled sufficiently below its softening range so that the dentition appliance will hold its shape when ejected.

The inherent problems in a method of molding slow-release fluoride into a plastic human dentition appliance are overcome by the addition of a high-temperature solvent to the fluoridating material.

For instance, one problem inherent to the above-identified method is that the combination of moisture present in the plastic, or on the injection molding machine, with the fluoridating material produces hydrofluoric acid. Hydrofluoric acid is the most deadly acid known. Further, hydrofluoric acid can corrode the screw and the barrel of the injection molding machine. By pre-mixing the fluoridating material with a high-temperature solvent, the fluoride will be more evenly distributed throughout the dental appliance, thereby eliminating pockets of concentrated fluoride within and on the appliance that can produce hydrofluoric acid when mixed with saliva, which might burn tissue and discolor teeth. Also, by pre-mixing the fluoridating material with a high-temperature solvent, the problem of fluoride powder being retained in the screw of the injection molding machine, forming pockets of concentrated fluoride which produce hydrofluoric acid when mixed with moisture, is eliminated.

A further problem inherent to the method is the creation of spots in the molded plastic dental appliance by the fluoridating material, resulting from heating the fluoridating material above its high-temperature limit. This problem is eliminated by pre-mixing the fluoridating material with a high-temperature solvent.

By having a fluoridated material, such as slow-release fluoride, forming a part of the appliance as a result of being injection molded directly into the material or being absorbed by or formed in the plastic, rubber, etc., the fluoride is brought into direct contact with the tooth surfaces that can most be in need of preventing decay. The released fluoride mixes with the saliva and remains in contact with tooth surfaces and especially can be worked into the contacting area of adjacent teeth, to be absorbed by those areas of the teeth that most frequently decay.

Although such an oral appliance has wide-spread uses, it would be particularly advantageous to children in remote areas of third world countries who use the appliance constructed in accordance with the method of the present invention, as these children frequently do not have fluoridated water or any other way of obtaining fluoridation protection at an early formative age.

BRIEF DESCRIPTION OF THE DRAWINGS

FIG. 1 is a perspective view of a human dentition preformed and/or custom-made appliance constructed in accordance with the principles of the present invention;

FIG. 2 is a top plan view of the appliance of FIG. 1;

FIG. 3 is a view taken on line III—III of FIG. 2 and is partly in section and partly in elevation showing additional details of construction of the appliance;

FIG. 4 is a fragmentary cross-sectional view of the appliance of FIGS. 1–3, but showing how the appliance embraces the teeth of a user;

FIG. 5 is a somewhat schematic illustration of a reciprocating-screw injection molding unit which can be utilized to practice the steps of the herein disclosed invention.

DESCRIPTION OF THE PREFERRED EMBODIMENTS

While the principles of the present invention are applicable to all human oral appliances, including preformed and/or custom-made dentition appliances, it should be understood that I contemplate the term "oral appliances" to include anti-thumb sucking and pacifier-type devices. The invention is particularly related to dentition appliances which are injection molded from thermoplastic materials rather than from powdered self-curing acrylic. Thus, the dentition appliance illustrated in FIGS. 1-4 is one made by injection molding or heat forming of a sheet from a thermoplastic material which include the silicone resins, polyurethane resins, polyvinyl chloride, latex rubber, water blush polyvinyl chloride, polypropylene resins, polyethylene resins, polycarbonates, and nylons, and such other thermoplastics that can be softened at temperatures within the high-temperature limit of the high-temperature solvent.

For example, the mixture of the fluoridating material and the high-temperature solvent must be compatible and soluble in high-temperature molded plastics such as PVC (350° F.), polycarbonates (425° F.), and nylons (500° F.). The best high-temperature solvent for achieving the requisite compatibility and solubility in high-temperature molded plastics is a vegetable oil-based solvent. It is also contemplated that other molding processes using thermoplastic materials such as rotary molding and blow molding could be used.

The appliance shown by way of exemplifying the principles of the present invention is identified generally at 20 and is U-shaped in plan so as to conform to the typical human mouth configuration and is generally H-shaped in cross-section providing an upper or superior tooth receiving trough 22 and a lower or inferior tooth receiving trough 24. The sides of the troughs 22 and 24 are bounded by a lingual flange 26 which covers the rear of the teeth of the upper and lower arch and a labial and buccal flange 28 which covers the front of the teeth of both arches.

It will be understood that the positioner 20 can be made having only an upper trough 22 or a lower trough 24. It will further be understood that either or both of the troughs 22 and 24 may be provided with a plurality of tooth receiving depressions or sockets such as those shown in FIG. 2 at 22a, 22b, 22c, 22d, 22e, 22f, 22g and 22h.

The upper portion of the lingual flange 26 secures the lingual cingulum areas of the upper anterior teeth and the lingual surfaces of the lingual cusps of the upper posterior teeth, and covers a portion of the upper lingual gingival area. The lower portion of the lingual flange 26 generally embraces the cingulum area of the lower anterior teeth and lingual surface of the lingual cusps of the lower posterior teeth and also extends over a portion of the lower lingual gingival tissue.

The lower labial and buccal flange 28 covers the labial and buccal surfaces of the lower anterior and posterior teeth and also extends over a portion of the lower labial and buccal gingival tissue while the upper portion of the labial and buccal flange 28 covers the entire labial and buccal surfaces of the upper anterior and posterior teeth and also embraces a small portion of the upper gingival tissue.

The various pockets such as 22a through 22h in the appliance are made so that the teeth are snugly embraced. There is an isthmus 30 which joins the lingual and buccal or labials halves of the appliance and is generally formed to resemble the normal relaxed clearance between the teeth, thereby enabling all of the occlusal and incisal surfaces of the teeth to be in contact with the appliance at any one time when occlusal pressure is applied.

Variations in the shape and thickness of the isthmus 30 and the pockets 22a -22h inclusive are illustrated by comparing the cross-sectional portions of FIGS. 3 and 4.

The present invention is particularly directed to an injection molding process. Generally, injection molding is a process that converts small pellets of thermoplastic resins called molding powders, into shaped articles, in this instance a dentition appliance adapted to be used with deciduous dentition or mixed dentition or permanent dentition. As noted, it would also be possible to form the thermoplastic resins into sheets that can then be reformed over models of teeth.

Since most injection machines are made to work with molds that part in a single plane when opening, the articles are designed to be conveniently ejected from such molds.

Although equally applicable to custom-made or heat-vacuum processes, the injection molding process follows the principal steps, namely, the feed pellets or molding powders are selected so they can be melted. Further, as contemplated in most injection molding methods, the melt is injected into a relatively cool mold, and the molding is chilled sufficiently below its softening range so that it will retain its shape when ejected.

For many years, resin was melted in injection machines by being rammed through a heated cylinder with a metal core called a torpedo. Eventually it was realized that conduction heating is not only slow, but also burns the plastic. Accordingly, many injection molding machines today use the screw-plasticating principle borrowed from the extruder art and adapted the same to injection molding. For purposes of illustration, such a machine is shown in FIG. 5 of the drawings. Thus, there is a hydraulic motor shown at 40 which rotatively drives a screw 41 through a spline 42. A hopper 43 feeds material into a melt chamber 44. A non-return valve is shown at 46 and accumulated melt is received in a compartment identified at 47 having a nozzle 48 at the end thereof. An injection piston 49 is axially movable on the spline 42.

In this machine, the screw 44 rotates rapidly for part of the molding cycle while the melt just previously injected into the chilled mold cools and freezes and the part is ejected. The mold is shown at 50 and it will be understood that the mold halves are configured to form the orthodontic or human dentition appliance 20.

As the mold closes, screw rotation ceases and a hydraulic ram thrusts the screw forward to inject the collected melt into the waiting mold. As this occurs, the nozzle of the machine makes high pressure contact with the sprue bushing of the mold, sealing the connection.

The injection molding machine of FIG. 5 is similar to the exemplary machine illustrated and described in the Modern Plastics Encyclopedia 1988 pages 7 and 8.

In accordance with the principles of the present invention, it is contemplated that a base material of thermoplastic resin will be charged into the hopper 43, however, before accomplishing that charge, there is admixed with the base material a charge of a mixture, including a fluoridating material and a high-temperature solvent, to form a pre-fluoridated mixture.

A typical fluoridating material is sodium fluoride, stannous fluoride, sodium monofluorophosphate, acidulated phosphate fluoride, amino fluoride, stannous chlorofluoride, potassium fluoride, magnesium fluoride, potassium trifluorostannite, stannous hexafluorozirconate, titanium fluoride, ammonium fluoride, fluoride glass ionomer or calcium fluoride or any other source of fluoride and/or tin. The fluoridating material is mixed with a high-temperature solvent to form a mixture that is then tumbled with the base material in concentrations varying from 0.01 mg. to 200 mg. per milliliter or 0.01% to 70% by weight (0.02 to 10% F. ion). Preferably, the high-temperature solvent is a vegetable oil-based solvent.

The most typical heat-resistant fluoride is sodium fluoride, although calcium fluoride is generally recognized as slower at releasing fluoride ions.

Any form of plastic or rubber used in the mouth and moldable by injection molding or heat/suction methods at temperatures within the high-temperature limit of the high-temperature solvent would be suitable as a base material. Thus, beads or small pellets of thermoplastic resin, called molding powders, could include any thermoplastic material selected from the class of silicone resins, polyurethane resins, polyvinyl chloride, latex rubber, water blush polyvinyl chloride, polypropylene resins, polyethylene resins, polycarbonates, nylons and any other plastic resins which are injection moldable to form human dentition appliances compatible with the human mouth.

After the base material is admixed with a charge of the above-identified mixture to form a pre-fluoridated mixture, the pre-fluoridated mixture is melted at softening temperatures within a range having an upper limit not exceeding the stability limits of the high-temperature solvent and at a lower limit sufficient to soften and plasticize the base material to form a melt.

As shown in FIG. 5, the pre-fluoridated mixture is shown at 60 in the hopper and is melted in the chamber 44 of the injection molding apparatus. In accordance with the operation of the machine, the melt is accumulated in the melt chamber 47.

In actual operation, it has been found that sodium fluoride is stable and retains its stability at temperatures up to 350° F. Moreover, most of the thermoplastic base materials referred to hereinabove and suitable for making orthodontic appliances plasticize or melt at temperatures in excess of 200°. For example, the melting temperature of PVC and polypropylenes in 350° F. Further, the melting temperature of polycarbonates is 425° F., while that of nylons is 500° F. Under the circumstances, it will be appreciated that the step of melting the pre-fluoridated mixture can be accomplished in accordance with this invention at temperatures within a range of 200° F. to 500° F.

With the melt accumulated in chamber 47, it is then injected into the relatively cool mold 50 which has molding recesses shaped to form a molding in the configuration of the orthodontic appliance or human dentition appliance 20 illustrated and described in connection with FIGS. 1-4. The molding is then chilled sufficiently below its softening range so that the appliance will hold its shape when ejected from the mold 50.

Since children are oftentimes asked to wear a dentition appliance that is made of soft resilient plastic for from one to several hours each day, or perhaps all night, while sleeping, the present invention beneficially accomplishes a slow release of fluoride which leaches out of the appliance as it is worn. The fluoridating material is heat stabile so that as the child or user wears the appliance, the fluoride leaches out of the appliance and becomes mixed with fluids in the mouth, particularly within the area between the dentition appliance and the surfaces of the teeth.

Since the buccal, labial, lingual and occlusal surfaces of the teeth come into direct contact with the appliance and the fluids of the mouth and remain for from 20 minutes to several hours each day, without being washed away by saliva, there exists an ideal climate to preventively fluoride the teeth as the appliance is used, especially since the appliance is adjacent to the surfaces of the teeth.

The principles of the present invention are particularly applicable to appliances or anti-thumb sucking and pacifier-type devices intended for use by children in remote areas of third world countries who use these appliance frequently, but do not have fluoridated water or any other way of obtaining fluoridation protection at an early formative age.

Stannous (tin) compounds, especially with fluorides also have a bacteriostatic characteristic and lessen periodontal problems and plaque formation around teeth and by being squeezed in and around the gums will prevent periodontitis and its associated problems, particularly by slow release and long contact of fluoride and tin with tooth and gum areas.

A recharge of fluoride and tin may be given to the appliance periodically or it can be an alternate method of delivery by soaking the appliance in the fluoride (and tin) compound. Certain areas of the appliance can also be soaked such as only around the tooth areas by placing the chemicals into the sockets and allowing the chemicals to be absorbed into the soluble-type (blush) plastic. In this way, the fluoride chemicals are mostly present at the tooth surface and not on the cheek surface so irritation on the cheeks is avoided. After several hours of soaking, the appliance is rinsed and dried and ready to be used in the mouth. Absorption of fluoride ion can be accelerated by giving the appliance a positive electrical charge when soaking, and when placed in the mouth, the appliance can be reversed and given a negative charge while the body may receive a positive charge from simple batteries.

Although various modifications might be suggested by those versed in the art, it should be understood that I wish to embody within the scope of the patent warranted hereon all such modifications as reasonably and properly come within the scope of my contribution to the art.

I claim as my invention:

1. A method of molding an appliance for being received in the mouth, comprising the steps of:
   mixing a fluoride material with a high-temperature solvent to form a mixture, the high-temperature solvent being heat-resistant up to 500° F.;
   tumbling a charge of base material in the mixture to form a pre-fluoridated mixture, whereby the fluoride contained in the pre-fluoridated mixture is evenly distributed over the charge of base material;
   melting the pre-fluoridated mixture at softening temperatures to form a melt, wherein melting the pre-fluoridated mixture occurs within a high-temperature limit of the high-temperature solvent to sufficiently soften and plasticize the charge of base material; and
   molding said melt into a configuration to fit within a human mouth.

2. A method according to claim 1, wherein the step of molding said melt into a configuration to fit within a human mouth further comprises the steps of:
   injecting the melt into a relatively cool mold-shape to form a molding in a configuration of a generally U-shaped orthodontic appliance to fit a configuration of a human mouth, said molding being generally H-shaped in cross-section with an isthmus portion, a side of the isthmus portion being vertical flanges, and outer flange being a labial-buccal flange, a interior flange being a lingual flange, and an occlusal surface between the vertical flanges having formed therein a plurality of individual sockets, each to receive a tooth; and chilling the molding sufficiently below its softening so that the appliance with hold its shape when ejected.

3. A method according to claim 2, wherein the step of injecting the melt into a mold further comprises screw-plasticating the melt into the mold.

4. A method according to claim 1, wherein the high-temperature solvent is a vegetable oil-based solvent.

5. A method according to claim 1, wherein said charge of base material is chosen from the group consisting of soft resilient synthetic thermoplastic material, thermoplastic rubber, and thermoplastic stiff plastic material, and wherein said charge of base material plasticizes at temperatures lower than the high-temperature limit of the high-temperature solvent.

6. A method according to claim 1, wherein the fluoride material is selected from the group consisting of finely ground sodium fluoride, liquid sodium fluoride, finely ground calcium fluoride, and liquid calcium fluoride.

7. A method according to claim 6, wherein the concentration of fluoridating material varies from 0.1 mm to 200 mm per milliter.

8. A method according to claim 6, wherein the concentration of fluoridating material varies from 0.1% to 70% by weight.

9. A method according to claim 1, wherein the step of melting the pre-fluoridated mixture occurs at temperatures within a range of 200° F. to 500° F.

* * * * *